United States Patent [19]
Martin

[11] Patent Number: 5,898,475
[45] Date of Patent: Apr. 27, 1999

[54] PRECISION FRAGRANCE DISPENSER APPARATUS

[76] Inventor: David A. Martin, 11422 Willow Gardens Dr., Windermere, Fla. 34786

[21] Appl. No.: 08/812,798

[22] Filed: Mar. 6, 1997

Related U.S. Application Data

[63] Continuation-in-part of application No. 08/492,401, Jun. 19, 1995, Pat. No. 5,610,674.

[51] Int. Cl.⁶ .................................................. G03B 21/32
[52] U.S. Cl. .............................................. 352/85; 352/40
[58] Field of Search .......................................... 352/85, 40

[56] References Cited

U.S. PATENT DOCUMENTS

| | | | |
|---|---|---|---|
| 2,540,144 | 2/1951 | Stern | 352/85 |
| 2,562,959 | 8/1951 | Stern | 352/85 |
| 2,562,960 | 8/1951 | Stern | 352/85 |
| 2,813,452 | 11/1957 | Laube | 352/85 |
| 3,795,438 | 3/1974 | Westenholz et al. | 352/85 |
| 5,610,674 | 3/1997 | Martin | 352/85 |

*Primary Examiner*—Russell Adams
*Attorney, Agent, or Firm*—William M. Hobby, III

[57] ABSTRACT

A method of dispensing fragrances includes selecting a fragrance dispenser apparatus having have a plurality of fragrance dispensers each having a fragrance release portion positioned for dispensing a fragrance to a predetermined area and having a source of pressurized gas connected to each fragrance dispenser and a gas pressure control mechanism connected between the source of pressurized gas in each of the plurality of fragrance dispensers and connected for receiving dispensing signals to selectively control the release of a pressurized gas, such are air, to individual fragrance dispensers for selectively dispersing different fragrances. Each selected fragrance dispenser is positioned adjacent the end of a pressurized gas tube and has a housing having an absorbent material therein supporting a fragrance absorbed in the material. The method includes the step of activating the selected fragrance dispenser apparatus gas pressure control mechanism to apply a predetermined volume of gas for a predetermined time period to at least one gas pressure tube through the remote fragrance dispenser absorbent material into the air around the fragrance dispenser to thereby disperse a fragrance laced gas at a predetermined location. The gas pressure control can be computer activated to control the remote dispensing of a gas laced with fragrance through pulses of pressurized gas. The selected housing can also have one or more membranes over the ends thereof which membranes allow the escape of a fragrance laden gas only at a predetermined gas pressure and otherwise blocking the egress of the fragrance therethrough.

15 Claims, 3 Drawing Sheets

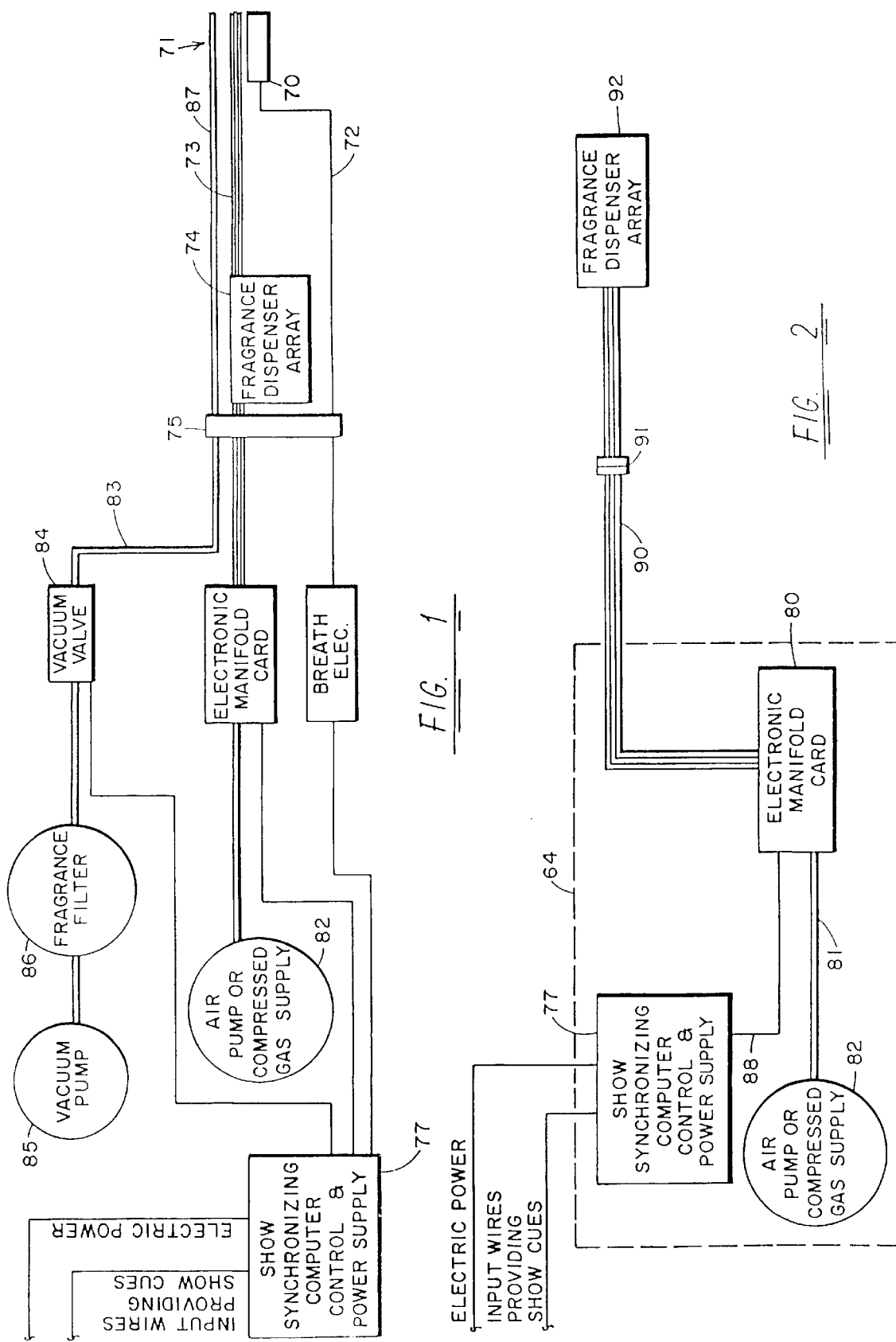

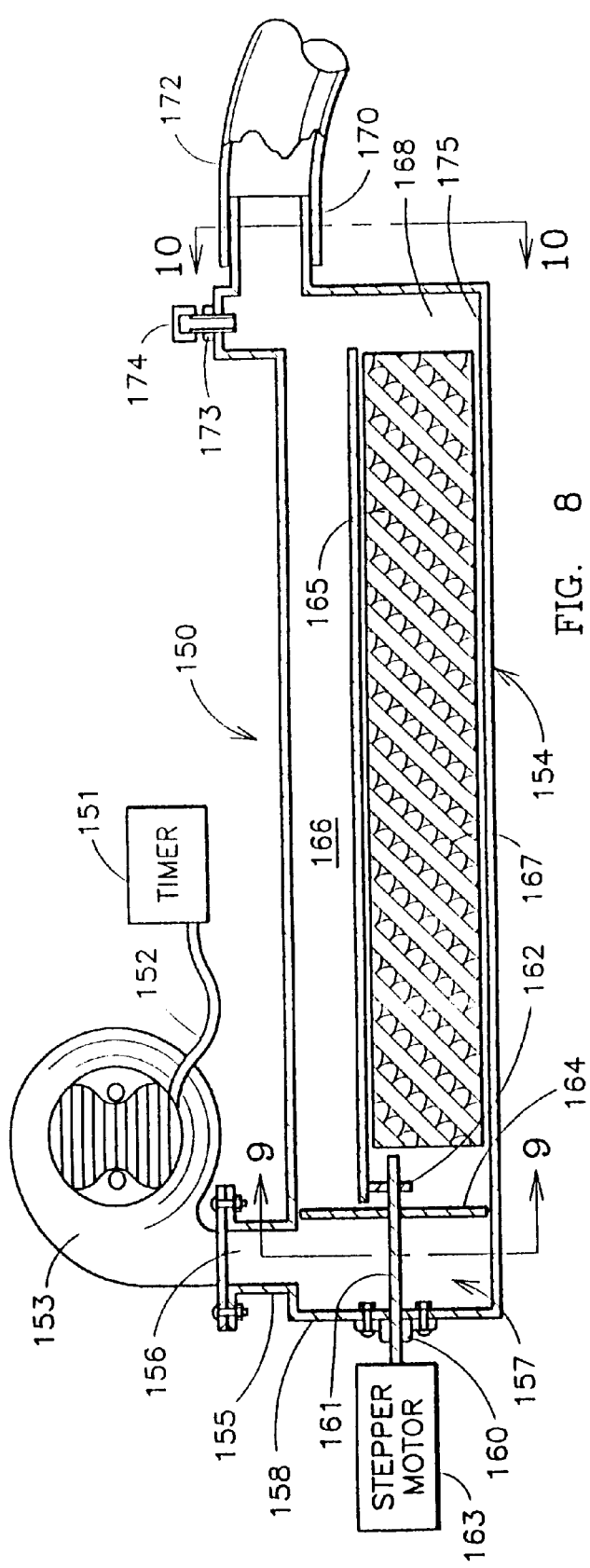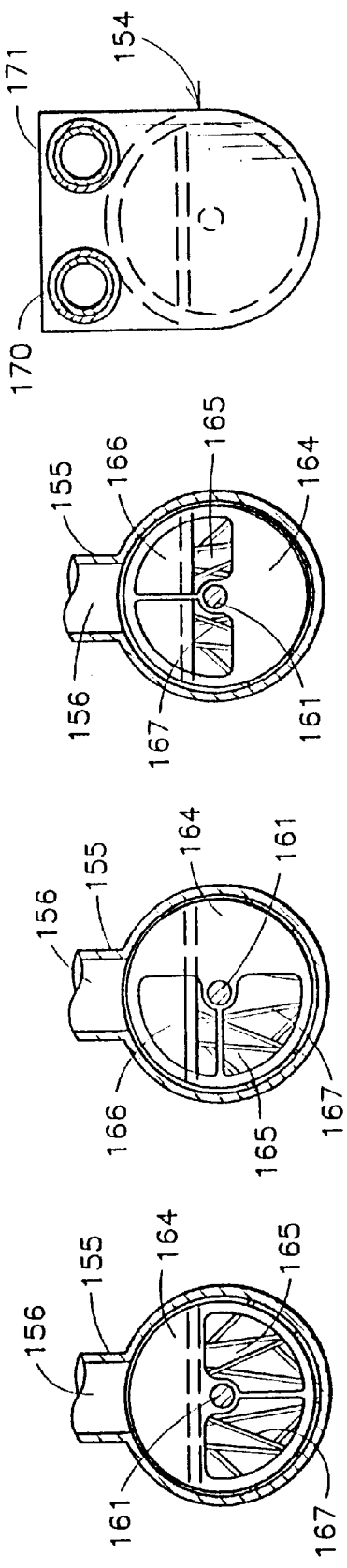

PRECISION FRAGRANCE DISPENSER APPARATUS

This invention is a continuation in part of my prior patent application Ser. No. 08/492,401 filed Jun. 19, 1995, now U.S. Pat. No. 5,610,674.

BACKGROUND OF THE INVENTION

This invention relates to a precision method and apparatus of dispensing fragrances and especially to a method and apparatus for filling large spaces with fragrances as well as dispensing fragrances suitable for use with outdoor Christmas trees, food fragrances to attract customers, or to mask unpleasant odors.

Some fragrance dispensing applications call for filling large spaces with fragrance and changing infrequently. One example is theme park ride systems that move guests through small themed rooms that require a different constant fragrance in each room to enhance the show. Other examples include evergreen fragrance for outdoor artificial Christmas trees, food fragrances to attract passing customers to a restaurant, or pleasant fragrances to mask unpleasant odors at a nursing home. One problem with filling large spaces is the difficulty in controlling concentration. A simple way to regulate fragrance concentration in the constant high volume air flow is needed to broadly disperse the generated fragrance. The present invention achieves this capability with a modified fragrance dispenser.

Precision fragrance dispensing is made directly to an individual and is coordinated with the viewing of a motion picture or television or to the viewing of an image in virtual reality or in computer games so that the viewer can realistically experience the full effect or illusion of being a part of or physically responding to the environment depicted by the viewed image and the accompanying audio. Existing theater systems and television and computer games and virtual reality generally are provided with a visual image along with the audio used in connection with the visual image. Past attempts, however, at incorporating the addition of smell to the overall viewing environment have not generally been successful and have not been widely accepted. One of the reasons for the lack of acceptance is the difficulty of providing smell to an individual user with any precision without providing the dispensed spell to a large area and to the problem of dissipating one smell and feeding a second smell as the scenes being viewed change. The smell sensation loses its effect and does not tend to provide the more accurate smells that attend any particular scene being viewed.

One prior art patent which attempts to provide a combination of a viewing chair and sense stimulating means for use in motion picture television theaters is provided in U.S. Pat. No. 3,628,829 to Hellig and includes a seat with arm rests having a back which terminates into a hood over the chair. The chair includes means for rocking the chair in various directions as well as means for vibrating the chair and an odor producing system associated with the chair which includes odor conducting conduits and means for moving air through the odor producing conduits towards the face of the spectator seated in the chair. The chair includes air passageways and exit ports for directing a fragrance towards various portions of the spectator's body and a system for feeding the fragrance to the air passageways and exhausting the odors around a chair for removing the odors. The Hellig system also includes a loudspeaker associated with the hood of a chair. This odor producing system attempts to direct the odors and the flow of fragrances to the area around the user's head and nose and then exhausts it from the area around the user's head and maintains the odors by partially enclosing the head. This, however, has had limited success because of the inability to precisely govern the dispensing of the various smells at precise moments and due to the delay in removing the generated odor in the area of the user's head.

The present invention is directed towards an apparatus for the precision dispensing of fragrance to a large volume area with precision control of the fragrance dispensed. A method and apparatus also provide for precision fragrance dispensing in small amounts to an area remotely controlled with pressurized gas signals.

SUMMARY OF THE INVENTION

A precision large volume fragrance dispenser is provided having a housing which has a plurality of passageways formed therein and has an input plenum at one end thereof and an output plenum at the other end thereof. The output plenum in turn has an output therefrom for dispensing a fragrance. One or more of the passageways has fragrance holding means, such as an absorbent material therein and an opening for adding a fragrance thereto. A source of pressurized gas, such as an air compressor, is connected to the housing input plenum for forcing gas thereinto and through each of the plurality of passageways so that some of the forced air is passing through passageways having a fragrance therein while some is passing through a passageway without any obstruction to the flow of gas. A gas control mechanism, such as a rotatable baffle, is mounted at one end of the passageways for controlling the amount of flow of pressurized gas through each of the plurality of passageways to thereby mix air and fragrance laden air in the output plenum for the control concentration depending upon the baffling of each of the passageways. Rotation of the gas control mechanism, such as with an electric stepping motor, will rotate the baffles to close off different portions of each passageway to vary the ratio between the gas passing through the fragrance holding passageway and the unobstructed passageways.

A method of dispensing fragrances includes selecting a fragrance dispenser apparatus having have a plurality of fragrance dispensers each having a fragrance release portion positioned for dispensing a fragrance to a predetermined area and having a source of pressurized gas connected to each fragrance dispenser and a gas pressure control mechanism connected between the source of pressurized gas in each of the plurality of fragrance dispensers and connected for receiving dispensing signals to selectively control the release of a pressurized gas, such are air, to individual fragrance dispensers for selectively dispersing different fragrances. Each selected fragrance dispenser is positioned adjacent the end of a pressurized gas tube and has a housing having an absorbent material therein supporting a fragrance absorbed in the material. The method includes the step of activating the selected fragrance dispenser apparatus gas pressure control mechanism to apply a predetermined volume of gas for a predetermined time period at least one gas pressure tube through the remote fragrance dispenser absorbent material into the air around said fragrance dispenser to thereby disperse a fragrance laced gas at a predetermined location. The gas pressure control can be computer activated to control the remote dispensing of a gas laced with fragrance through pulses of pressurized gas. The selected housing can also have one or more flexible membranes the ends thereof which membranes allow the escape of a fragrance laden gas only upon a predetermined gas pressure and otherwise blocking the egress of the fragrance therethrough. The selected source of air can be an oil-free air compressor or a compressed gas in a container which is remotely located and controlled to direct pressured gas through a tube to the remote fragrance dispenser.

BRIEF DESCRIPTION OF THE DRAWINGS

Other objects, features, and advantages of the present invention will be apparent from the written description and the drawings in which:

FIG. 1 is a schematic for a precision fragrance dispenser;

FIG. 2 is a schematic for a second precision fragrance dispenser;

FIG. 8 is a sectional view of a large volume fragrance dispenser;

FIG. 9 is a sectional view taken on the line 9—9 of FIG. 8 and having the baffle in one position;

FIG. 9A is the sectional view of FIG. 9 having the baffle rotated to a different position;

FIG. 9B is the sectional view of FIG. 9 having the baffle rotated to a third position; and FIG. 10 is a sectional view taken on the line 10—10 of FIG. 8.

DESCRIPTION OF THE PREFERRED EMBODIMENT

Figure 3:
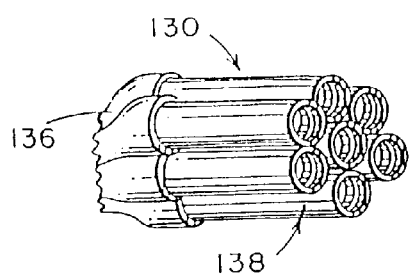
FIG. 3 is a perspective view of a plurality of fragrance dispensers bound together.

Referring to the drawings, FIGS. 1 and 2, two schematics of a precision fragrance dispenser are illustrated. In FIG. 2, an end dispenser dispenses directly therefrom. In FIG. 1, a remote sensor 70 is connected on the dispensing end 71 and has electric conductors 72 connected to the sensor 70 while the individual fragrance lines 73 are connected to the dispensing end 71 for dispensing fragrances adjacent a remote location. The fragrance dispenser array 74 is positioned in the line 73 and passes through a quick disconnect 75 which also disconnects the electrical conductor 72 containing the feedback signals from the breath sensor. The breath sensor electronics module 76 is located in the line and is connected to the show synchronizing computer control 77. Similar control wires 78 are connected between the computer 77 and the electronic manifold card 80 which also has the compressed gas line 81 connected from a compressed gas source 82. A vacuum line 83 is connected to a vacuum valve 84 and to a vacuum pump 85 and through a fragrance filter 86 on one end and through the quick disconnect 75 and through a vacuum line 87 to the dispensing end 71. The vacuum line withdraws fragrances after they have been dispensed by the individual fragrance gas lines 73 under pressure from the pressurized gas source 82 responsive to the breath sensor 70.

FIG. 2 shows another embodiment of a schematic in accordance with FIG. 1 having the computer control 77 along with a compressed gas source 82 and an electronic manifold card. Compressed gas is supplied from the source 82 through the gas line 81 to the electronic manifold card 80.

Control wires 88 connect the computer control to the manifold card 80 which controls the dispensing of the individual gas lines 90 through a quick disconnect 91 to the fragrance dispenser array 92.

The schematic of FIG. 1 dispenses the fragrances midway in the gas flow line while the schematic of FIG. 2 dispenses the fragrance at one end of the gas flow line. The electronic manifold card 80 can utilize any of the commercially available boards to control the gas flow to select the fragrance dispenser. These cards provide individually controlled gas output ports from a common manifold gas supply using either 6, 12, or 24 volt DC solenoids controllable directly from a computer through a standard 24 pin connector and can be manually controlled if desired. The gas supply 82 can be any source of clean and dry gas supplied in compressed bottles, liquid gas used in aerosols, or through an air compressor. Compressed bottled gas can be $CO_2$ nitrogen or any dry gas or merely compressed air. An air compressor can be utilized which provides an oil free air since the supply gas is breathed by the user. For video games, a low cost oil free tropical fish compressor is available. The gas is regulated to about 2 to 5 psi in a typical fragrance dispenser in accordance with the present invention.

FIGS. 3 through 7 show several embodiments of fragrance dispensers. FIG. 3 is a fragrance dispenser 130 is illustrated having an isolation membrane 131 placed upstream of the fragrance location while an isolation membrane 132 is placed downstream of the fragrance. A porous material 133 holds the fragrance material therein. The membrane 132 has a perforation 134 therein. The membrane opening 134 remains closed and seals the fragrance within the body 135 in the absence of pressure and dispenses the fragrance only upon the application of pressure through the gas lines 136. The membrane 131 has a slot perforation 137 to allow the incoming air under pressure to pass therethrough and through the porous material 133 holding the fragrance therein. As seen in FIG. 8, a plurality of the dispenser 138 are attached together having a plurality of gas lines 136, one attached to each of the dispensers to provide dispensing of a plurality of different fragrances upon pressurized gas input from each line 136 being selectively applied to the desired dispenser.

Figure 4:
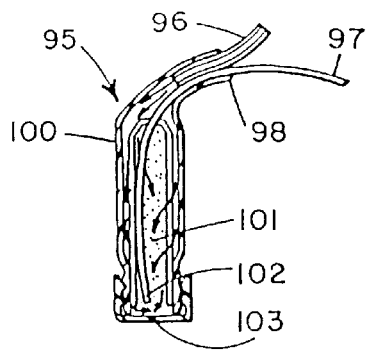
FIG. 4 is a sectional view of a fragrance dispenser.

FIG. 4 is a fragrance dispenser tip 95 is illustrated for use with frequent replenishment capability and has a tube 96 for the gas entering the dispenser and a tube 97 for fragrance laden gas exiting the dispenser. The tube 97 and body 100 are made of a material which does not permit fragrance migration through the tube wall or chemically react with the fragrance, such as glass and some plastics, as well as some non-reactive metals. Polyamide capillary tubing, made by Micropolyx in Chattanooga, Tenn., is particularly well suited for tube 97. An adhesive 98 seals one or more tubes to the body 100 of the dispenser tip 95. The body 100 holds the fragrance therein and allows a gas, such as air being fed thereinto, to become fragrance laden before dispensing. Arrows in the figure indicate the route taken by the incoming gas as it mingles with the fragrance fumes in the reservoir material 101. The reservoir material 101 holds the quantity of a fragrance, which can be polymer pellets or an absorbent or porous material, such as vermiculite, paper, cotton, carbon particles or any open celled polymer foam, or synthetic absorbent which holds substantial quantities of fragrance for a gradual release into the surrounding gas atmosphere. An exit port 102 allows for the removal of the fragrance laden gas and is positioned at the furthest end away from the inlet tube 96. A removal cap 103 is attached over the end of the body 100 and allows for replacement of the fragrances even through a non-removable cap could also be provided, such as an elastomer cover, which could have the fragrances refilled with a syringe.

Figure 5:
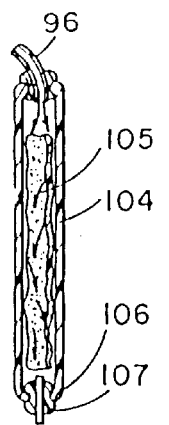
FIG. 5 is a sectional view of a second fragrance dispenser.

FIG. 5 is a sectional view that shows a similar fragrance dispenser to that in FIG. 5 having the gas input tube 96 extending into a body 104 having the reservoir material 105 therein laden with a fragrance but having the tube for the fragrance laden gas exiting the dispenser through the tube 106 at the opposite end of the housing 104 and the adhesive 107 for sealing the container body 104.

Figure 6:
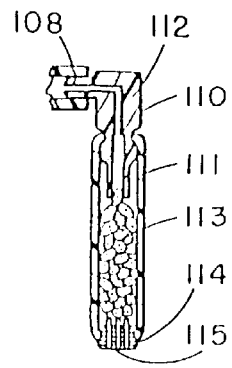
FIG. 6 is a sectional view of another embodiment of a fragrance dispenser.
Figure 7:
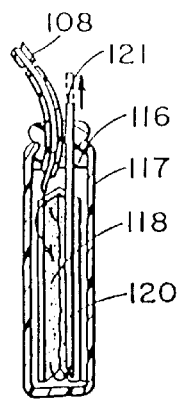
FIG. 7 is a sectional view of another embodiment of a fragrance dispenser.

Referring to FIGS. 6 and 7, a replaceable disposal fragrance dispenser is illustrated in FIG. 6. The gas tube 108 feeds a gas into the tube cap 110 which in turn is attached to the tube body 111. The gas is fed through the molded tube cap 110 passageway 112 into the container 111 which has an absorbent or porous reservoir material 113 therein and an end cap 114 having a plurality of apertures 115 therethrough for dispersing fragrance laden gases. The sectional view in FIG. 6A has the gas line 108 feeding through the molded cap 116 into the body 117 of the dispenser. The absorbent or porous reservoir material 118 has a gas passing therethrough and into a TEFLON tube 120 having an extension 121 extending from the container 117 through the cap 116.

The method of dispensing fragrances herein includes selecting a fragrance dispenser apparatus, FIG. 2, having a plurality of fragrance dispensers 92 each having a fragrance release portion positioned for dispensing a fragrance to a predetermined area and having a source of pressurized gas 82 connected to each fragrance dispenser and a gas pressure control mechanism 80 connected between the source of pressurized gas 82 in each of the plurality of fragrance dispensers 92 and connected for receiving dispensing signals to selectively control the release of a pressurized gas, such are air, to individual fragrance dispensers, FIGS. 3–6, for selectively dispersing different fragrances. Each selected fragrance dispenser 92 is positioned adjacent the end of a pressurized gas tube 90 and has a housing having an absorbent material therein supporting a fragrance absorbed in the material. The method includes the step of activating the selected fragrance dispenser, FIG. 2, apparatus gas pressure control mechanism 80 to apply a predetermined volume of gas for a predetermined time period to at least one gas pressure tube 90 through the remote fragrance dispenser absorbent material into the air around the fragrance dispenser 92 to thereby disperse a fragrance laced gas at a predetermined location. The gas pressure control can be computer 77 activated to control the remote dispensing of a gas laced with fragrance through pulses of pressurized gas. The selected housing can also have one or more flexible membranes over the ends thereof which membranes allow the escape of a fragrance laden gas only upon a predetermined gas pressure and otherwise blocking the egress of the fragrance therethrough. The selected source of air can be an oil-free air compressor or a compressed gas in a container which is remotely located and controlled to direct pressurized gas through a tube to the remote fragrance dispenser.

Turning now to FIGS. 8, 9, 9A, 9B, and 10, an embodiment of a precision fragrance dispenser is illustrated for use in large volume areas, such as outside of a building or in an open area of a shopping mall. The dispenser 150 has a timer 151 connected through a conductor 152 to a bore 153. The bore 153 can be any source of compressed air, such as a squirrel cage blower or fan, an air compressor, a container of pressurized gas or the like. The bore 153 is connected to the fragrance dispenser housing 154 at a gas input 155 where the air enters the intake manifold 156 and an input plenum area 157. An end plate 158 covers the end of the plenum 157 and has an attached bearing 160 supporting a shaft 161 at one end while a bearing 162 supports the shaft at the other end thereof. Motor 163, which may be an electric stepper motor, is attached to the shaft 161 for rotating the shaft as the motor steps the shaft through 360 degrees of rotation. It will, of course, be clear that mechanical or manual rotation of the shaft 161 can also be utilized for controlling the fragrance dispenser. The shaft 161 has a baffle 164 attached thereto for rotation therewith, as seen in FIGS. 9, 9A and 9B. The housing 154 has a plurality of passageways 165 and 166. Passageway 165 is a fragrance containing passageway having an absorbent material 167 therein which can hold a liquid fragrance so that gas or air passing through the passageway 165 will become fragrance laden as it passes into an output plenum 168. Passageway 166 is unobstructed so that unobstructed gas or pressurized air can pass therethrough without collecting any fragrance and enters into the output plenum 168.

The baffle 164 is shaped and rotated to block most or any portion of either the passageway 165 or 166 so that the amount of fragrance being delivered to the output plenum 168 is controlled by the amount of air being forced through one or both passageways. The air is blocked off from the fragrance passageway 165, as shown in FIG. 9B, and most of the air is forced through the unobstructed passageway 166 and there is minimum fragrance output in the plenum 168 and in the housing output 170 and 171. When the baffle 164 is rotated, as shown in FIG. 9, it blocks the total passageway 166 and forces all of the pressurized gas to pass through the passageway 165 and through the absorbent material 167 having a fragrance therein so that the fragrance reaching the plenum 168 is at maximum setting. When the baffle 164 is rotated, as in FIG. 9A, halfway between the positions, it forces roughly equal amounts of air through the passageway 166 and 165. It will be noted that a larger area of the passageway 165 is open in this view but the air is also obstructed by having to pass through the absorbent material 167. The fragrance laden air and the pure air passing through the passageways are mixed in the plenum 168 and are driven out of the outputs 170 and 171. The outputs may have tubes 172 attached thereto for directing the fragrance laden gas to any desired position in the embodiment shown. In the figures, a fragrance filling port 173 may have a cap 174. The fragrance is poured into the opening 173 and onto the floor area 175 of the housing 154 where it is absorbed by the absorbent material 167 which then wicks the fragrance thereinto. The wicking material 167 can be any material desired, such as a paper or a cotton material or an open cell foam or even an absorbent particulate as desired without departing from the spirit and scope of the invention.

The precision fragrance dispenser of FIGS. 8–10 is especially suitable for precision fragrance dispensing within a large volume space, such as the outdoors, and provides for fine adjustments for varying the amount of fragrance being dispensed which can be done remotely or by computer control by driving the stepping motor 163 to adjust the baffles. A fragrance dispenser of this type is especially suited for producing evergreen fragrance for outdoor artificial Christmas trees or for food fragrances to attract customers to a restaurant or to mask unpleasant odors at a nursing home. There has been difficulty in controlling the concentration of a fragrance in an area of this type and this fragrance dispenser provides a simple way to regulate the fragrance concentrate while using a constant high volume air flow to broadly disperse the generated fragrance.

It should be clear at this time that a precision fragrance dispenser and method of dispensing fragrances has been provided in which the delivery of fragrances can be precisely controlled. A plurality of small tubes is used to deliver small localized fragrance dispensing to a remote area from a source of pressurized gas or the control of the release of the gas into individual tubes using pressurized gas signals. Accurate control of fragrance dispensing in a large volume area is accomplished by controlling the constant flow of air through different passageways. The accurate dispensing of a fragrance in this manner reduces the amount of fragrance needed to produce the desired sensory effect on individuals. The dispensers advantageously produce the fragrance from the fragrance soaked supporting materials by passing pressured air or gas therethrough. The present invention should not be construed as limited to the forms shown which are to be considered illustrative rather than restrictive.

I claim:

1. A precision large volume fragrance dispenser comprising:
    a fragrance dispenser housing, said housing having a plurality of passageways therethrough and having an input at one end thereof and an output at the other end thereof and one said passageway having fragrance holding means therein for holding a selected fragrance therein;
    a source of pressurized gas connected to said housing for forcing a pressurized gas through each of said plurality of passageways;
    a fragrance in said fragrance holding means of one said passageway having a fragrance holding means therein whereby pressurized gas passing therethrough will evaporate fragrance therein;
    a variable gas control mechanism mounted at said input of said passageways for proportioning the amount of flow of pressurized gas flowing into and through each of said plurality of passageways to thereby provide a mix of gas and fragrance laden gas in said output to thereby control the concentration of fragrance in said housing output gas in said output plenum by said gas pressure control mechanism.

2. A precision large volume fragrance dispenser in accordance with claim 1 in which said gas control mechanism has a proportioning plate positioned at one end of said housing passageways to proportion the volume of gas passing into each passageway to thereby vary the ratio of gas passing through the passageways and the fragrance to air mixture in the output.

3. A precision large volume fragrance dispenser in accordance with claim 2 in which said gas control mechanism proportioning plate is a rotatable plate having a plurality of openings therein positioned to cover varying portions of said passageways to vary the amount of gas passing into each passageway to thereby vary the ratio of gas passing through the passageways.

4. A precision large volume fragrance dispenser in accordance with claim 3 in which said gas control mechanism rotatable proportioning plate has a motor coupled thereto for remotely varying said proportioning plate to cover portions of said passageways to vary the ratio of gas passing through the passageways.

5. A precision large volume fragrance dispenser in accordance with claim 4 in which said gas control mechanism motor is an electric stepper motor for repositioning said proportioning plate in steppes.

6. A fragrance dispenser for use with synchronized visual images in accordance with claim 1 in which each said fragrance holding means in one said passageway is an absorbent material supporting a fragrance absorbed therein.

7. A precision large volume fragrance dispenser in accordance with claim 6 in which said fragrance holding means is paper for absorbing a fragrance.

8. A precision large volume fragrance dispenser in accordance with claim 7 in which said source of pressurized gas includes an air blower for compressing air.

9. A precision large volume fragrance dispenser in accordance with claim 7 in which said source of pressurized gas is a compressed gas container filled with compressed air.

10. A fragrance dispensing method comprising the steps of:
    selecting a fragrance dispenser apparatus having a source of pressurized gas connected to a gas pressure control mechanism and having a plurality of gas pressure tubes connected to said gas pressure control mechanism for separately applying pressured gas to each of said plurality of gas pressure tubes responsive to said gas pressure control mechanism, and having a plurality of fragrance dispensers each coupled to one of said plurality of gas pressure tubes adjacent the end of said tube and each having a housing having an absorbent material therein for supporting a fragrance absorbed therein;
    activating said fragrance dispenser apparatus gas pressure control mechanism to apply a predetermined volume of gas for a predetermined time period at least one gas pressure tube through the remote fragrance dispenser absorbent material into the air around said fragrance dispenser to thereby disperse a fragrance laced gas at a predetermined location.

11. A fragrance dispensing method in accordance with claim 10 in which the step of selecting a fragrance dispenser having a source of pressurized gas includes selecting an air compressor for compressing air.

12. A fragrance dispensing method in accordance with claim 11 in which the step of selecting a fragrance dispenser housing having a membrane covering one end thereof selected to allow the egress of a fragrance laden gas only at a predetermined positive pressure.

13. A fragrance dispensing method in accordance with claim 12 in which the step of selecting a fragrance dispenser housing having a second membrane covering the other end of the housing to allow the ingress of a gas from said pressured gas line only at a predetermined positive pressure.

14. A fragrance dispensing method in accordance with claim 13 in which the step of selecting a fragrance dispenser having an absorbent material of cotton.

15. A fragrance dispenser comprising:
    a source of pressurized gas;
    a gas pressure control mechanism connected to said source of pressurized gas;
    a plurality of gas pressure tubes connected to said gas pressure control mechanism for separately applying pressured gas to each of said plurality of gas pressure tubes responsive to said gas pressure control mechanism; and
    a plurality of fragrance dispensers each coupled to one of said plurality of gas pressure tubes adjacent the end of said tube and each having a housing having an absorbent material therein for supporting a fragrance absorbed therein, whereby a remote gas signal disperses a predetermined fragrance by the volume of pressurized gas passing through the absorbent material to evaporate fragrance therein.

* * * * *